United States Patent [19]

Ferre

[11] Patent Number: 4,824,788

[45] Date of Patent: Apr. 25, 1989

[54] HUMIDITY CHAMBER FOR IMMUNOPEROXIDASE STAINING

[76] Inventor: Penelope J. Ferre, 1416 2nd St. North, St. Petersburg, Fla. 33704

[21] Appl. No.: 117,844

[22] Filed: Nov. 9, 1987

[51] Int. Cl.$^4$ .............................................. C12M 1/22
[52] U.S. Cl. ..................... 435/298; 435/301
[58] Field of Search ............... 435/287, 310, 311, 289; 220/22; 126/20, 369; 34/201, 202

[56] References Cited

U.S. PATENT DOCUMENTS

| | | | |
|---|---|---|---|
| 1,083,783 | 1/1914 | Weber | 126/369 |
| 2,806,123 | 9/1957 | Steinbock, Jr. | 126/20 |
| 3,165,450 | 1/1965 | Scheidt | 435/301 |
| 3,715,280 | 2/1973 | Farmer, III | 435/301 |
| 3,837,560 | 9/1974 | Kuchuris et al. | 220/22 |
| 3,860,489 | 1/1975 | Cooper, III | 435/310 |
| 3,886,047 | 5/1975 | Billups, Jr. | 435/298 |
| 4,087,327 | 5/1978 | Feder | 435/287 |
| 4,598,050 | 7/1986 | Brown | 435/301 |
| 4,668,633 | 5/1987 | Walton | 435/298 |
| 4,728,607 | 3/1988 | Dorn et al. | 435/298 |

FOREIGN PATENT DOCUMENTS

| | | | |
|---|---|---|---|
| 2305697 | 10/1976 | France | 126/441 |
| 2563232 | 10/1985 | France | 435/298 |

Primary Examiner—James C. Yeung
Attorney, Agent, or Firm—Walter J. Monacelli

[57] ABSTRACT

The humidity chamber for immunoperoxidase staining comprises a rectangular chamber with a tight removable or opening lid, which encloses a grid positioned a fixed distance from the chamber bottom on which grid the glass slides holding specimens may be positioned without tilting. The grid is 40–90 percent open so as to permit ventilation between bottom and upper positions of the chamber so as to maintain constant humidity.

6 Claims, 1 Drawing Sheet

HUMIDITY CHAMBER FOR IMMUNOPEROXIDASE STAINING

BACKGROUND OF THE INVENTION

1. FIELD OF THE INVENTION

This invention relates to an incubation chamber in which a number of glass slides on which specimen samples have been deposited and a staining solution dropped thereon for immunoperoxidase reaction. More specifically it relates to such a chamber in which the slides are supported on a removable grid through which air may circulate and excess liquid may fall to the bottom of the chamber. Still more specifically it relates to such a chamber which may be closed tightly or temporarily sealed to prevent changes in humidity.

2. STATE OF THE PRIOR ART

Laboratories performing this type of immunoperoxidase have been using makeshift equipment or using commercial equipment which is inadequate to handle the number of slides desired or may be unsatisfactory in one or more respects.

One type of incubating device is that shown in U.S. Pat. No. 4,384,193 which is complicated and expensive. Moreover this device requires exact positioning of a limited number of slides.

A number of other patents show various types of chambers for the handling or storage of specimen slides. These include U.S. Pat. Nos. 3,726,767, 3,756,393, 4,077,515 and 4,589,551.

Accurate Chemical & Scientific Corporation of Westbury, New York markets an incubation chamber with a tray raised from the bottom of the chamber which has a number of ridges on which slides are rested and has a number of openings to allow ventilation. However, the tray does not have sufficient rigidity, and the ridges provide an uneven surface for the slides. There are not sufficient openings to allow for good ventilation or air circulation, and if the number or size of the openings are increased, this would give even poorer rigidity.

OBJECTS OF THE INVENTION

It is an object of this invention to provide a chamber simple in structure which can perform the various functions described above.

It is also an object of this invention to provide a chamber which can accommodate a sufficient number of specimen slides.

It is still a further object of this invention to provide a chamber which can allow excess liquid from the slides to flow to the bottom of the chamber.

It is a still further object of this invention to provide a chamber which has sufficient open space between upper and lower regions of the chamber so that a constant humidity can be maintained during the storage or reaction period.

It is a still further object to provide a smooth or even supporting means in a single plane so that the slides will not be tilted.

It is a still further object of this invention to provide a chamber which has a supporting structure for the slides which can be easily removed for cleaning of this supporting structure and for cleaning of the chamber.

It is a still further object of this invention to provide a support for a greater number of slides which has good rigidity.

Other objects will become manifest upon reading the description of this invention given herein.

SUMMARY OF THIS INVENTION

In accordance with the present invention, it has been found that these objects are accomplished by a rectangular chamber of appropriate height, preferably of a transparent plastic having a lid thereon capable of maintaining a tight seal on the contents of the chamber and having a removable grid inside the chamber on which an appropriate number of slides may be positioned. The grid is supported by a supporting means which holds it an appropriate distance from the bottom of the chamber. Preferably this supporting means comprises a number of projections of various types which extend from the walls of the chamber. These projections may be a narrow shelf which extends at least partially around the walls of the chamber and on which the grid may rest. This may also comprise a number of pegs of uniform height which are adhered upright to the walls of the chamber with the top ends of the pegs reaching to the appropriate height to support the grid. The pegs must have sufficient width or thickness to reach under the edge of the grid. Furthermore the width of the grid must be sufficient to reach the supporting pegs at the sides of the chamber. In any case the tops of the pegs or supporting means must be high enough off the bottom of the chamber to hold the grid at an appropriate distance from the bottom of the chamber.

An important feature of the grid is that it is largely open, preferably about 40-90% open, so that excess liquid may flow downward and air may circulate through the openings so as to provide uniform humidity. The grid is advantageously constucted of a series of longitudinal slats or strips and a series of lateral slats or strips. The strips are appropriately cut at intersecting portions so that longitudinal slats or strips may dovetail with lateral slats or strips and advantageously be glued together or fitted tightly so as to provide a rigid structure. The length of the longitudinal strips are designed to fit within the length of the rectangular chamber and the length of the lateral strips are designed to fit within the width of the rectangular chamber. The thickness of these strips is advantageously sufficient to give strength and rigidity to the grid. A grid having openings $\frac{1}{2}$ inch by $\frac{1}{2}$ inch is found very suitable with the strips having a depth of about $\frac{1}{2}$ inch and thickness of about 1/16" or $\frac{1}{8}$ inch.

Distances of about $\frac{1}{2}$ inch between slats is found suitable to give a smooth support for the slides and to provide maximum ventilation to provide uniform humidity.

A convenient size of chamber is one having dimensions about 12 inches by 24 inches by 4 inches with six 2.5 inch plastic pegs glued perpendicularly to the inside of the chamber. The bottom of each peg rests on the bottom of the chamber and the pegs may be spaced from each other, three on each of the longer sides of the chamber. The lid is preferably hinged to one of the side walls and is fitted to provide an air-tight seal when closed. However while a hinged cover is preferred, various other types of covers may be used which provide a tight seal.

Where reference is made to a "rectangular" chamber this is with regard to the view of the chamber looking down on the uncovered chamber or to a cross-section of the chamber made by the intersection of the chamber by a plane parallel to and above the bottom of the chamber.

By "rectangular" it is intended to include a square chamber.

Description of the invention may be facilitated by reference to the drawings.

SPECIFIC EMBODIMENT OF THE INVENTION

Figure 1:
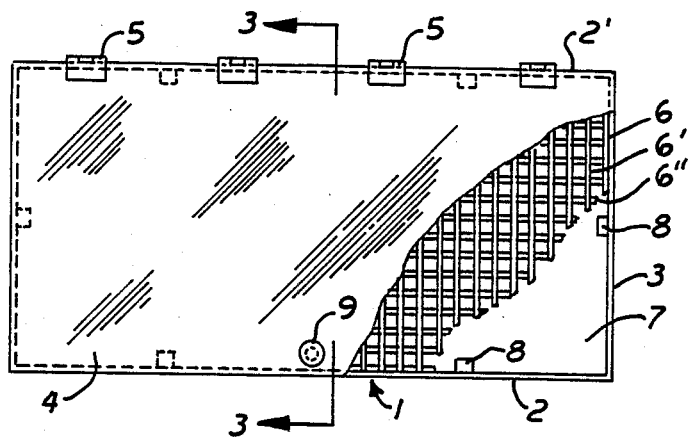
FIG. 1 is a top view of a preferred modification of the apparatus of this invention with partial views through the top lid and through the grid portion of the apparatus.
Figure 2:
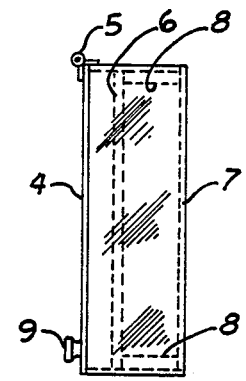
FIG. 2 is an end view of the apparatus of FIG. 1 taken with the apparatus resting on one of its longitudinal sides.
Figure 3:
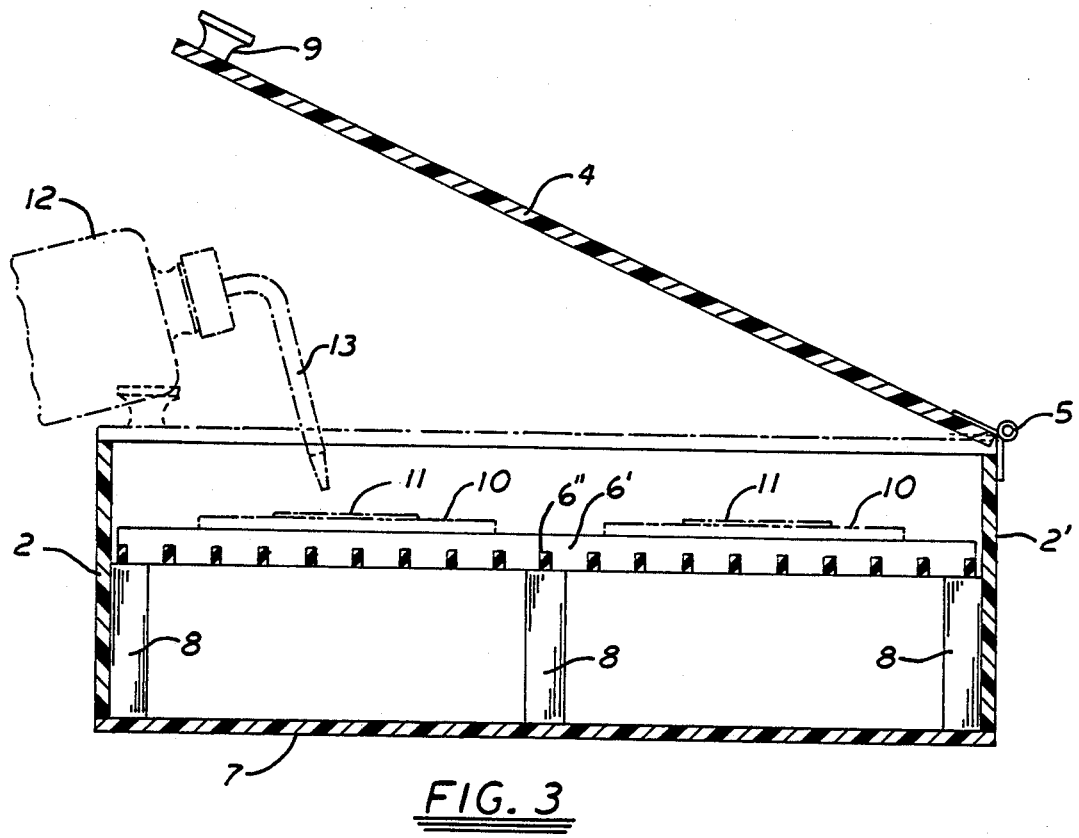
FIG. 3 is a cross-sectional view of the apparatus of FIG. 1 taken at line 3—3 and with the lid partially open.

The incubation chamber 1 has longitudinal side 2, lateral side 3, lid 4, attached by hinges 5 to the other longitudinal side 2'. Grid 6 is held above the bottom 7 by pegs 8 which are attached to the side walls of the chamber. Knob 9 is attached to the lid 4 to facilitate lifting the unhinged side thereof. In the cross-sectional view of FIG. 3 the lateral slats 6' are shown dovetailed with longitudinal slats 6". Glass slides 10 are shown in phantom positioned on grid 6 with specimen 11 thereon. Also in phantom is shown a squeeze bottle 12 with spout 13 used to apply a wash solution to the specimen on the glass slide. During incubation period drops of reagent may be dropped onto the specimens by a similar bottle or by an eye dropper type device.

Any liquid running off the glass slides may pass through the grid into the bottom of the chamber. Periodically, after the slides have been removed, the grid may be removed and both the grid and the chamber cleaned and washed preliminary to re-use.

As indicated above the chamber of this invention has various advantages, namely the glass slides are well supported and untiltable, the 40–90 percent open space in the grid provides adequate means of ventilation so that constant humidity is easily maintained. Moreover the grid is easily removed for cleaning thereof as well as for cleaning the chamber.

While certain features of this invention have been described in detail with respect to various embodiments thereof, it will of course be apparent that other modifications can be made within the spirit and scope of this invention, it is not intended to limit the invention to the exact details insofar as they are defined in the following claims.

The invention claimed is:

1. A humidity chamber in combination with a number of glass slides on which specimen samples have been deposited thereon and a staining solution dropped thereon for immunoperoxidase reaction, comprising:
    (a) a rectangular housing having four walls and a bottom wall tightly sealed together forming said humidity chamber, said chamber having an upper opening to provide access to said chamber;
    (b) a grid for supporting the glass slides within the chamber, said grid having a substantial open portion therein capable of being fitted within the four side walls, said grid comprising a series of longitudinal slats parallel to each other and spaced from adjacent longitudinal slats and a series of lateral slats parallel to each other and spaced from adjacent slats with the lateral slats positioned perpendicular to the longitudinal slats dovetailed to fit each other;
    (c) a supporting means for supporting said grid and spaced from said bottom wall forming upper and lower regions of the chamber so that a constant humidity can be maintained between upper and lower regions of the chamber and allowing any excess solution from the glass slides to drain through the grid to the bottom region of the chamber; and
    (d) a top providing a cover and tight seal for said upper opening of said chamber.

2. The apparatus of claim 1 in which the top edges of both the longitudinal and lateral slats are in the same plane.

3. The apparatus of claim 2 in which said top is hinged to one of the said side walls.

4. The apparatus of claim 3 in which the spacing between said slats provides 40–90 percent open space in said grid.

5. The apparatus of claim 2 in which the spacing between said slats provides 40–90 percent open space in said grid.

6. The apparatus of claim 1 in which the spacing between said slats provides 40–90 percent open space in said grid.

* * * * *